United States Patent [19]
Miyake et al.

[11] Patent Number: 5,736,100
[45] Date of Patent: Apr. 7, 1998

[54] CHEMICAL ANALYZER NON-INVASIVE STIRRER

[75] Inventors: Ryo Miyake, Tsukuba; Koichi Tsuzuki, Tsuchiura; Isao Yamazaki; Hideo Enoki, both of Ibaraki-ken; Hiroshi Mitsumaki, Mito, all of Japan

[73] Assignee: Hitachi, Ltd., Tokyo, Japan

[21] Appl. No.: 531,199

[22] Filed: Sep. 19, 1995

[30] Foreign Application Priority Data

Sep. 20, 1994 [JP] Japan .................... 6-224768

[51] Int. Cl.$^6$ ............................. G01N 37/00; B01F 11/02
[52] U.S. Cl. ..................... 422/64; 422/63; 435/43; 435/47; 435/174; 366/127
[58] Field of Search ...................... 422/63, 64, 67, 422/99, 100; 436/43, 49, 174, 179, 180, 183; 366/110, 111, 113, 114, 116, 108, 127

[56] References Cited

U.S. PATENT DOCUMENTS

| | | | |
|---|---|---|---|
| 2,407,462 | 9/1946 | Whiteley . | |
| 2,468,538 | 4/1949 | Benioff | 366/113 |
| 2,702,692 | 2/1955 | Kessler | 366/113 |
| 3,292,910 | 12/1966 | Martner | 366/110 |
| 3,325,976 | 6/1967 | West . | |
| 3,700,089 | 10/1972 | Halbartschlager et al. | 198/1 |
| 3,807,704 | 4/1974 | Janzen et al. | 366/111 |
| 3,873,071 | 3/1975 | Tatebe | 366/113 |
| 3,912,450 | 10/1975 | Boucher | 21/54 A |
| 4,451,433 | 5/1984 | Yamashita et al. . | |
| 4,528,159 | 7/1985 | Liston . | |
| 4,764,021 | 8/1988 | Eppes | 366/127 |
| 4,774,055 | 9/1988 | Wakatake et al. | 422/64 |
| 4,815,978 | 3/1989 | Mazza et al. | 435/4 |
| 4,836,684 | 6/1989 | Javorik et al. | 366/114 |
| 4,872,353 | 10/1989 | Orr, Jr. et al. . | |
| 4,930,898 | 6/1990 | Miller-Ihli | 366/109 |
| 5,484,573 | 1/1996 | Berger et al. | 422/128 |

FOREIGN PATENT DOCUMENTS

| | | |
|---|---|---|
| 0 423 925 A1 | 4/1991 | European Pat. Off. . |
| 17 85 229 | 12/1958 | Germany . |
| 29 24 806 A1 | 1/1981 | Germany . |
| 43 05 660 A1 | 9/1993 | Germany . |
| 57-28182 | 2/1982 | Japan . |
| 63-20026 | 1/1988 | Japan . |
| 5-317820 | 12/1993 | Japan . |

OTHER PUBLICATIONS

"Ultrasonically Induced Microtransport", by R.M. Moroney et al., Berkeley Sensor & Actutator Center, Department of EECS and the Electronics Research Laboratory, University of California at Berkeley, 1991.

"Promotion of Heat Transfer by Straight Acoustic Streaming" by Hideo Kimoto (Faculty of Engineering Science, Osaka University, Toyonaka, 560), Jan. 1989.

Natural Convection from Downward Facing Horizontal Plate to Water (Effect of Acoustic Streaming), by M. Fujii, et al.Jul. 1992, (Partial Translation).

"Development of stirring element employing piezoilectric element—Principle and stirring characteristic thereof", JJCLA, vol. 17, 1992, p. 357, (Partial translation to be provided).

*Primary Examiner*—Long V. Le
*Attorney, Agent, or Firm*—Antonelli, Terry, Stout, & Kraus, LLP

[57] ABSTRACT

A chemical analyzer has turn tables respectively carrying reaction vessels, sample containers and reagent containers disposed thereon in circular rows. A sample pipetting mechanism and a reagent pipetting mechanism are provided to transfer predetermined amounts of sample and reagent solution from a sample container and from a reagent container into a reaction vessel. The thus transferred sample and reagent solution are mixed in the reaction vessel by a stirrer comprising a piezoelectric element which is disposed in non-contacting relationship to the sample and reagent solution in the reaction vessel and is electrically energized to generate a sound wave which causes a circulating flow of the reagent solution in the reaction vessel whereby the sample and the reagent solution are mixed in a non-invasive manner.

23 Claims, 4 Drawing Sheets

CHEMICAL ANALYZER NON-INVASIVE STIRRER

BACKGROUND OF THE INVENTION

The present invention relates to chemical analysis and, more particularly, to a chemical analyzer provided with a stirrer operative to mix a sample and a reagent solution in a reaction vessel in a non-invasive manner.

U.S. Pat. No. 4,451,433 discloses an example of the conventional chemical analyzers. The chemical analyzer disclosed in the U.S. patent has a calorimetric analysis section for analyzing and measuring the protein content of blood or the components of urine and an ion analysis section for analyzing the ion content of blood. The analyzer has a processing capacity of more than several hundreds of tests per hour. Larger analyzers have been designed to perform more than 9,000 tests per hour. In order to increase the processing speed of the calorimetric analysis section, in particular, a large number of reaction vessels are provided in a row on a turn table disposed in the upper surface of the chemical analyzer so that samples are successively mixed, reacted and measured in overlapped process steps. The analyzer mainly comprises automatic sample and reagent feeding mechanisms for automatically feeding samples and reagents into successive reaction vessels, an automatic stirrer for mixing samples and reagents in the reaction vessels, a meter for measuring the physical characteristics or properties of the samples during or after reactions thereof with the reagents, an automatic washing mechanism for sucking and discharging the thus measured samples from reaction vessels and then washing the vessels, and a controller for controlling the respective steps of operation. The automatic stirrer for mixing samples and reagents has a stirring stick member designed to be lowered into each reaction vessel beyond the liquid level therein to cause a swirling flow in the reaction vessel, a motor for rotating the stirring stick member, a washing vessel in which the stirring stick member is to be washed, and a drive mechanism for moving the stirring stick member reciprocally between the washing vessel and the reaction vessel.

In the field of chemical and medical analysis, there is a great demand for a great decrease or minimization of the quantities of samples and reagents to be tested. More specifically, as the analysis items are increased, the quantity of each sample to be used for each of the analysis items is decreased. In addition, analysis by use of very small amounts of sample and reagent, which has conventionally been regarded to be a high level analysis, such as an NDA analysis in which a sample is very rare and cannot be prepared in a large amount, has now become to be conducted in a routine manner. Moreover, as the required levels of analyses are raised, expensive reagents are usually used for the analyses. From the view point of running costs for analyses, there is a great demand for decrease or minimization of the quantities of reagents to be used for such analyses. In the fields of manufacture of medicines and biological technology, moreover, it has become important to mix very small quantities of reagents or to prepare a sample by use of very small amounts of materials.

In the prior art, a stirring member such as a stick or screw has been used to mix liquids in reaction vessels. After the liquids have been mixed, the mixture is adhered to the stirring member and carried over to a test of a succeeding material, which causes a contamination and adversely affects the succeeding test.

Recently, hospitals which conveniently utilize chemical analyzers tend to be equipped with other various machines and devices. Thus, there is a demand for reduction in the sizes of the chemical analyzers.

SUMMARY OF THE INVENTION

It is a first object of the present invention to provide a chemical analyzer which is structured to prevent the carry-over of liquids which occurs in the prior art analyzer when liquids are mixed.

It is a second object of the present invention to provide a chemical analyzer of a reduced size.

In order to achieve the first object, the present invention provides a chemical analyzer including a reaction vessel, means for feeding a sample into said reaction vessel through an upper opening thereof, means for feeding a reagent into said vessel through the upper opening thereof, and means for measuring a physical property of said sample during or after reaction of said sample with said regent, the improvement which comprises a sound wave generating means disposed outside said reaction vessel for generating sound wave toward said reaction vessel.

So as to achieve the second object, the present invention provides a chemical analyzer comprising a first turn table with a plurality of reaction vessels disposed thereon in a circular row, a second turn table with a plurality of sample containers disposed thereon in a circular row, each sample container containing a sample to be tested, a third turn table with a plurality of reagent containers disposed thereon in a circular row, each reagent container containing a quantity of reagent solution, sample feeding means operative to transfer a sample from one of said sample containers into one of said reaction vessels through an upper opening thereof, reagent feeding means operative to transfer a reagent solution from one of said reagent containers into said one reaction vessel through an upper opening thereof, and means for measuring a physical property of the sample contained in said one reaction vessel during or after reaction of said sample with a reagent contained in said one reaction vessel, the improvement which comprises a sound wave generating means so disposed as to be outside each reaction vessel for generating sound wave toward the reaction vessel.

The primary reason for the carry-over occurred in the prior art is that a stirring stick or screw was used to mechanically mix a sample and a reagent fed into a reaction vessel.

In the present invention, the sound wave generating means is provided outside the reaction vessel to generate sound wave toward the reaction vessel. The sound wave thus generated acts through the reaction vessel to stir the sample and the reagent in the reaction vessel and, therefore, eliminates the necessity for the stirring stick or screw used in the prior art chemical analyzer to mechanically stir a sample and a regent in a reaction vessel.

In the prior art, moreover, the size of the chemical analyzer was governed mainly by the diameters of the turn table for carrying thereon a plurality of reaction vessels, of the sample turn table for carrying thereon a plurality of sample containers and of the reagent turn table for carrying thereon a plurality of reagent containers. The diameters of these turn tables are determined based on the sizes of respective reagent vessels and sample and reagent containers. Because it is difficult to reduce the number of reaction vessels processed per unit of time, it is required that the sizes of the reaction vessels and the sample and reagent containers be reduced. However, the sizes of the reaction vessels and the sample and reagent containers are determined based on the quantities of sample and reagent to be contained in each reaction vessel, each sample container and each reagent container, it is no longer possible to reduce the sizes of such vessels and containers.

The quantities of sample and reagent to be contained in such vessels and containers are not the quantities essentially required for analyses but the quantities determined for the purpose of mechanical stirring operation carried out by a stirring stick or screw. Namely, because a mechanical stirring operation cannot be well performed if smaller amounts of sample and reagent are fed into a reaction vessel, the sample and the reagent fed into a reaction vessel are of quantities unnecessarily larger for a chemical analysis and a measurement.

According to the present invention, the stirring operation is conducted not by any mechanical member but by sound wave such that the materials to be mixed in a reaction vessel are not contacted by any mechanical stirring member. In the mechanical stirring operation, certain amounts of sample and reagent are required to enable a stirring stick or the like to mix the sample and reagent mechanically. In the present invention, because stirring is carried out by means of sound wave, the materials to be mixed in a reaction vessel are stirred by their own movements in the reaction vessel. According to the present invention, therefore, reduced amounts of sample and reagent are enough for a stirring operation carried out in a reaction vessel. Thus, a sample and a reagent to be fed into a reaction vessel can be of the quantities required only for a chemical analysis and measurement, with a result that the sizes of the reaction vessels and the sample and reagent containers can be reduced to enable the turn tables for the vessels and containers to be of reduced diameters. Accordingly, the present invention provides an advantage that the size of the chemical analyzer in its entirety can be reduced.

Uses of ultrasonic wave for the purpose of stirring operations are disclosed in the following publications, although the stirring operations are not for chemical analyzers:

Japanese Unexamined Patent Publication No. 57-28182 discloses a method of mixing a liquid crystal and a polychroism coloring matter in which a container containing the liquid crystal and the coloring matter is closed by a lid member and then the container is subjected to ultrasonic wave to vibrate the container at a high frequency.

A Publication, "Promotion of Beat Transfer by Acoustic Flow", Japan Acoustic Society Journal, Vol. 45, No. 1(1989), teaches the use of a straight acoustic flow which acts from outside, in a manner similar to a forced flow, to promote heat transfer in a heated material.

A publication, "Ultrasonically Induced Microtransport", 1991 IEEE, pages 277–282, discloses a fluid conveyance means comprising piezoelectric film provided on a bottom wall surface of a vessel to generate transverse progressive wave.

The attempt to use acoustic flow in a stirrer of a chemical analyzer inevitably encounters the problem that the top of each reaction vessel must be opened in order to assure that a sample and a reagent can be introduced into the vessel so as to be mixed together therein. It has been found through research that, if ultrasonic waves are imparted to the reaction vessel thoughtlessly or in an uncontrolled manner, the materials being mixed in the reaction vessel are thrown out of the vessel through the upper opening thereof.

In order to solve this problem, each of the preferred embodiments of the invention to be described hereinunder has a piezoelectric element which is properly positioned relative to a reaction vessel so that the materials to be mixed in the reaction vessel are prevented from being subjected uniformly to the same magnitude of ultrasonic wave. In other words, the piezoelectric element is positioned in relation to the reaction vessel such that a flow is caused in the materials to be mixed in the reaction vessel to prevent the materials from being moved together upwardly in the vessel and thrown out through the upper opening thereof.

DESCRIPTION OF THE PREFERRED EMBODIMENTS

Figure 1:
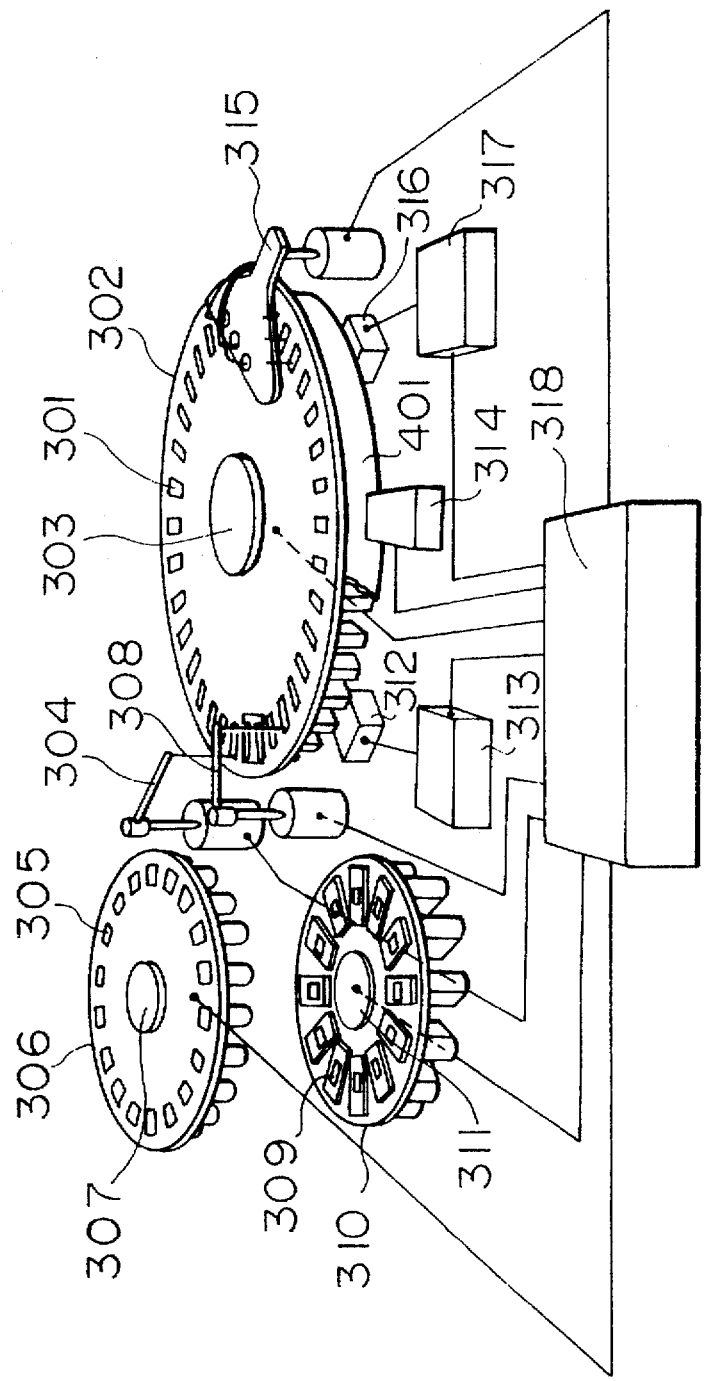
FIG. 1 is a schematic perspective view of an embodiment of the chemical analyzer according to the present invention.
Figure 2:
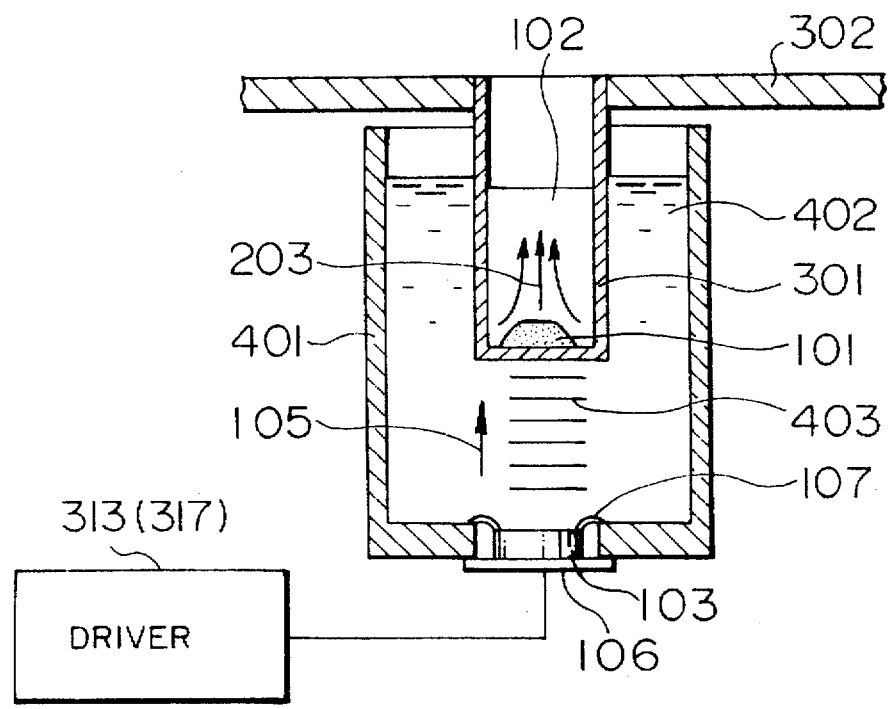
FIG. 2 is an enlarged fragmentary sectional view of the chemical analyzer shown in FIG. 1 showing a non-invasive stirrer provided in the analyzer.

Referring to FIGS. 1 and 2, a chemical analyzer includes a plurality of reaction vessels 301 fixed to a vessel holding turn table 302 along an outer periphery thereof. The turn table 302 is rotatable by a first table driving section 303 so that the reaction vessels 301 are revolved thereby about the axis of the turn table 302. An automatic sample feeding mechanism 304 for supplying samples to the reaction vessels 301 and an automatic reagent feeding mechanism 308 for supplying different kinds of reagent solutions to the reaction vessels 301 are disposed adjacent to the outer periphery of the turn table 302. In order that the automatic sample feeding mechanism 304 may be successively supplied with samples, a plurality of sample cups or containers 305 are mounted on a sample carrying turn table 306 which is connected to a second table driving section 307 for rotation thereby so that the sample containers 305 are revolved about the axis of the turn table 306. In order that the reagent feeding mechanism 308 may supply different kinds of reagent solutions to the reaction vessels 301, a plurality of reagent bottles 309 are mounted on a reagent bottle turn table 310 which is connected to a third driving section 311 for rotation thereby.

At a position where the automatic reagent feeding mechanism 308 discharges a reagent solution into a reaction vessel 301 on the vessel holding turn table 302, a non-invasive stirrer 312 and a driver 313 therefor are disposed so as to mix together the reagent solution thus discharged into the reaction vessel 301 and a sample therein. A measuring section 314 is disposed adjacent to the outer periphery of the vessel holding turn table 302 but spaced from the stirrer 312 to measure the physical properties of the liquids produced by reactions in the reaction vessels. At another position along the outer periphery of the vessel holding turn table 302, a washing mechanism 315 is disposed to suck reacted liquids from reaction vessels 301 and then feed washing liquid into the vessels to wash and clean the interiors of the vessels. Adjacent to the washing mechanism 315, a second non-invasive stirrer 316 and a driver 317 therefor are provided to cause convections in reaction vessels 301 to cause agitations therein for thereby increasing the efficiency of the washing and cleaning of the vessels.

The turn table driving sections 303, 307 and 311, the automatic sample feeding mechanism 304, the automatic reagent solution feeding mechanism 308, the drivers 313 and 317 for the two non-invasive stirrers 312 and 316, and the washing mechanism 315 are all electrically connected by controlling signal lines to a controlling section 318. The measuring section 314 is also electrically connected to the controlling section 318 by another controlling signal line. The vessel holding turn table 302 is rotated stepwise so that the reaction vessels 301 held thereby are moved about the axis of the turn table 302 stepwise.

Each of the non-invasive stirrers 312 and 316 is in the form of a piezoelectric element 103 mounted through a position adjuster 106 on the bottom of a water container 401 and electrically connected to the driver 313 or 317. The piezoelectric element 103 is positioned such that, each time when the reaction vessels 301 are stopped, one of the reaction vessels 301 is positioned above the piezoelectric element 103. The position adjuster 106 is provided to assure that, when the vessels 301 are so stopped, the one reaction vessel is positioned in vertical alignment with the piezoelectric element 103. However, the position adjuster 106 may be eliminated if the vessel holding turn table 302 is structured to precisely position one reaction vessel 301 in alignment with the piezoelectric element 103.

Referring particularly to FIG. 2, each reaction vessel 301 is fixed to the reaction vessel holding turn table 302 and contains a sample 101 and a reagent solution 102. The water container 401 mentioned hereinabove contains a quantity of water 402 kept at a constant temperature and is disposed under the turn table 302 such that an associated reaction vessel 301 is partially dipped into the constant temperature water 402. The water container 401 is so sized that the piezoelectric element 103 mounted on the bottom of the container 401 is disposed in non-contacting relationship with the bottom of the reaction vessel 301 received in the water container 401. The piezoelectric element 103 is driven by the driver 313 or 317 at a predetermined frequency.

In operation, the piezoelectric element 103 is driven by the driver 313 or 317 and vibrated thereby at a predetermined frequency in a direction indicated by an arrow 105 in FIG. 2. This vibration is propagated as a sound wave indicated by 403 through the water 402 in the container 401 until the sound wave 403 reaches the bottom of the reaction vessel 301. Thereafter, the sound wave 403 passes through the bottom wall of the reaction vessel 301 and arrives at the sample 101 and the reagent solution 102 contained therein. The sound wave 403 is propagated in the reagent solution in the vertical direction in the reaction vessel 301, so that there is caused an upward flow known as "acoustic straight flow" which is shown by arrows 203.

The reason why the upward flow is caused is believed to be that, when the sound wave is propagated in a fluid such as a solution in the direction of vibration, the viscosity and the volume viscosity of the fluid cause an absorption of the sound wave which in turn causes a difference or variation in the energy of the sound wave in the direction of the propagation thereof to thereby generate a pressure gradient in the fluid, as is discussed in a publication "Physical Acoustics", pages 265–330.

The generation of the acoustic straight flow 203 causes a vertical convection in the reaction vessel 301, so that the sample 101 is first lifted to the surface of the reagent solution 102 and then lowered along the inner peripheral surface of the vessel 301, whereby the sample 101 and the reagent solution 102 are stirred and mixed in the vessel 301. It is to be noted that this stirring and mixing operation is caused without any solid stirring member inserted into the reaction vessel 301. The velocity of the acoustic straight flow 203 is increased with increases in the sound absorption coefficient of the reagent solution, in the frequency of the vibration and in the amplitude of the vibration. It has been found through experimental tests that the condition for a remarkable occurrence of an acoustic straight flow in the reaction vessel 301 requires the piezoelectric element 103 to be vibrated at a velocity of at least $1\times10^{-4}$ m/s. It is unnecessary that the reaction vessel 301 is disposed in contact with the piezoelectric element 103.

Figure 3:
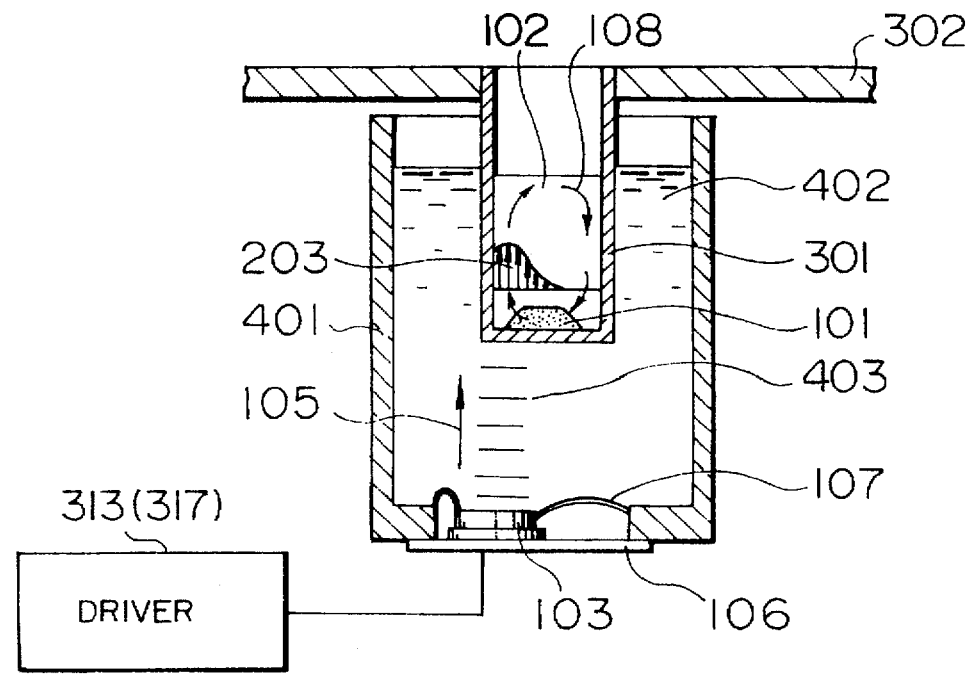
FIGS. 3–6 are similar to FIG. 2 but illustrate modified non-invasive stirrers, respectively.
Figure 4:
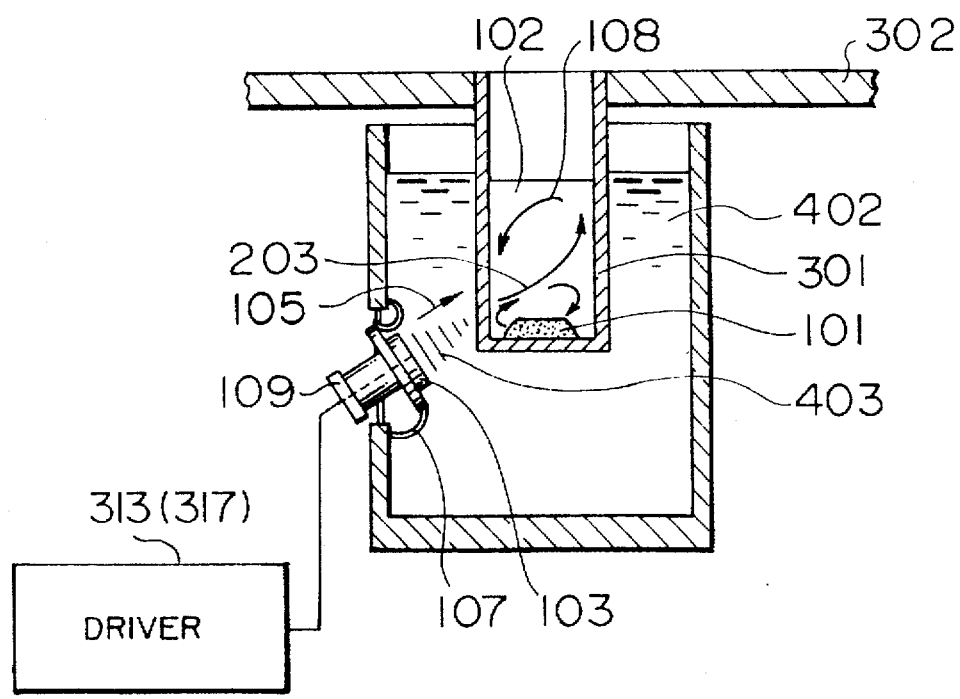
Figure 5:
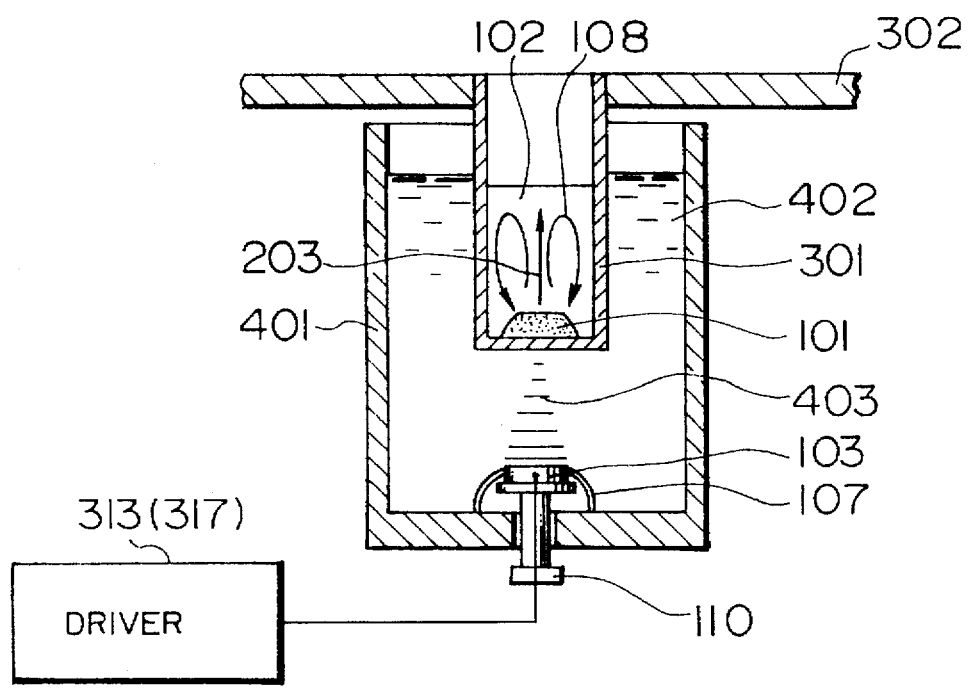

Referring now to FIGS. 3 through 5 which show modified arrangements of the non-invasive stirrers of the chemical analyzer according to the present invention, it is preferred that, in order to facilitate an efficient mixing and agitating operation in a short period of time, a circulating flow 108 be caused in the reaction vessel 301. In order that such circulating flow may be caused by an acoustic straight flow, it is preferred that a variation in the distribution of magnitude of the energy of the sound wave be established in a plane perpendicular to the direction of the propagation of the sound wave to assure that the magnitudes of straight flows caused in the direction of propagation of an ultrasonic wave are not uniform in the said plane. A difference in velocity between the straight flows causes a circulating flow. As a method of causing a variation in the energy magnitude distribution, the position adjuster 106 shown in FIG. 3 is so structured that the piezoelectric element 103 is disposed at a position offset from the center of the bottom of the water container 401 to assure that the zone through which the ultrasonic wave is propagated in the reaction vessel 301 is offset from the longitudinal axis of the reaction vessel, whereby the magnitude of the energy is largest in a zone adjacent to one side of the inner peripheral wall surface of the vessel 301, as shown by an acoustic straight flow 203 formed adjacent to the peripheral wall of the vessel 301, to cause a downward flow along the opposite side of the inner peripheral wall surface of the vessel 301. A sealing member 107 is disposed between the thus offset piezoelectric element 103 and the bottom of the water container 401.

In the modification shown in FIG. 4, the piezoelectric element 103 is mounted on the side wall of the water container. The angle of the piezoelectric element 103 is adjusted by an angle adjuster 109 so that an ultrasonic wave emitted by the piezoelectric element 103 is directed obliquely to a part of one side of the peripheral wall of the reaction vessel 301, whereby a variation in the energy magnitude distribution is established in the reaction vessel 301 to form a circulating flow 108 which starts from the one side of the peripheral wall of the vessel 301 to the opposite side thereof where the circulating flow 108 diverges and is returned to the one side of the vessel peripheral wall.

In the modification shown in FIG. 5, the distance of the forward or inner end face of the piezoelectric element 103 to the reaction vessel 301 is adjusted by a distance adjuster 110 such that the energy of the ultrasonic wave 403 is converged at the bottom wall of the reaction vessel 301 to assure that the magnitude of the energy is strongest in a small area or point in a plane which is located within the reaction vessel and is perpendicular to the direction of the propagation of the ultrasonic wave 403. This arrangement is also effective to establish a circulating flow 108 which rises from the central zone of the bottom of the reaction vessel 301 toward the surface of the reagent solution 102 and is then returned therefrom toward the bottom of the reaction vessel 301.

Figure 6:
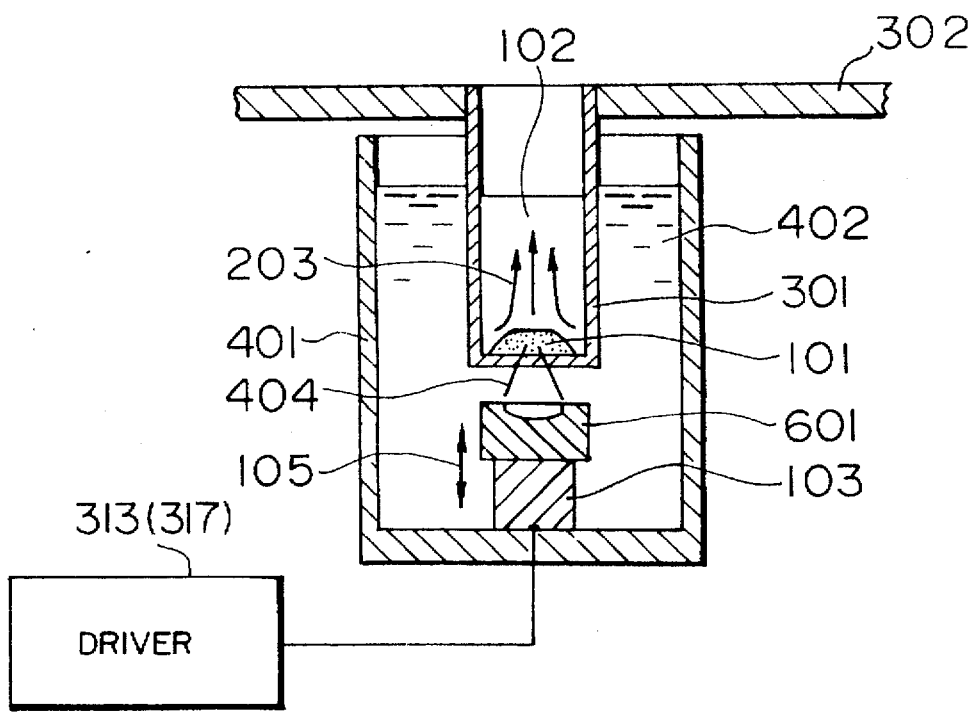

FIG. 6 shows a further modification to the stirrer shown in FIG. 2. The structure of the modified stirrer shown in FIG. 6 is basically similar to that of the stirrer shown in FIG. 2 but is provided with an acoustic lens 601 disposed in the path of propagation of the ultrasonic wave emitted by the piezoelectric element 103. The acoustic lens 601 is operative to gather the ultrasonic wave in the constant temperature water 402 so that the thus gathered ultrasonic wave passes as a sound wave 404 through the bottom of the reaction vessel and is condensed at a point adjacent to the sample 101 and the reagent solution in the reaction vessel. In a point adjacent to the sample 101, therefore, a vertically upwardly directed strong sound field is generated to form an acoustic straight flow 203 strong enough to lift the sample 101. The modified stirrer shown in FIG. 6, therefore, can be effectively applied to a case where a sample of large specific gravity and a high viscosity should be quickly stirred.

The chemical analyzer provided with one of the stirrers described above is controlled by the controller 318 and operates as follows:

First, the sample carrying turn table 306 is rotated to move a sample cup or container 305 with a sample contained therein to a predetermined position. The automatic sample feeding mechanism 304 then sucks the sample from the sample container 305, conveys the thus sucked sample and then discharges a predetermined quantity of the thus conveyed sample into a reaction vessel 301 on the vessel holding turn table 302. The first table driving section 303 is then actuated to rotate the turn table 302 and thus move the reaction vessel 301 to a predetermined position in which the automatic reagent feeding mechanism 308 is designed to feed a quantity of a reagent solution into the reaction vessel 301. The automatic reagent feeding mechanism 308 sucks from a reagent bottle 309 a reagent solution suited for an intended analysis item and then discharges a predetermined quantity of the thus sucked reagent solution into the reaction vessel 301. The stirrer 312 is actuated simultaneously with the discharge of the reagent solution into the reaction vessel 301 to agitate and mix together the sample and the reagent solution in the vessel 301.

After the mixing operation is finished, the vessel holding turn table 302 is rotated to move the reaction vessel 301 to a measuring station formed by the measuring section 314. The measuring section 314 measures the physical properties of the sample contained in the reaction vessel 301 fed to the measuring station. Thereafter, the reaction vessel 301 is moved to a washing station formed by the washing mechanism 315 and is washed and cleaned thereby. More specifically, the washing mechanism 315 sucks from the reaction vessel 301 the sample reacted with the reagent and then discharges a quantity of washing liquid into the reaction vessel 301. At the same time, the second stirrer 316 is actuated to cause a convection all over the entire quantity of the washing liquid fed into the reaction vessel 301 to thereby facilitate complete washing and cleaning of the interior of the reaction vessel.

The respective steps of operation described above are repeated for successive and different samples.

The described and illustrated embodiment of the chemical analyzer of the present invention can be operative to mix samples and reagent solutions in a non-invasive manner to thereby eliminate the prior art problem that liquid is taken out or carried over by a stirring stick. Another advantage of the described embodiment of the invention is that a measuring can be carried out for much reduced quantities of samples and reagent solutions. Moreover, because reaction vessels of reduced sizes can be used for mixing of samples and reagent solutions, the sample holding turn table 302 can be of a reduced size but capable of carrying as many reaction vessels as were carried by a sample holding turn table of the conventional chemical analyzer, with a resultant advantage that the chemical analyzer can be reduced in size with the capacity thereof kept unchanged. This will mean that, in the case where the chemical analyzer of the invention is structured to be of the same size as in the the prior art, the analyzer is able to hold and carry an increased number of reaction vessels and, thus, provides a remarkably increased sample-processing capacity. Further more, in the chemical analyzer of the described embodiment of the invention, the mixing of a sample and a reagent solution in a reaction vessel can be carried out at the position where the reagent vessel is fed into the reaction vessel. In other words, a feeding of a reagent solution into a reaction vessel and a mixing of the reagent solution with a sample in the vessel can be performed in one and the same position. Thus, the chemical analyzer of the described embodiment of the invention can eliminate the time which was needed in the prior art for the mixing and stirring. Further more, the second stirrer disposed at the washing and cleaning station is of a non-invasive type and provides an improved vessel-cleaning operation.

Figure 7:
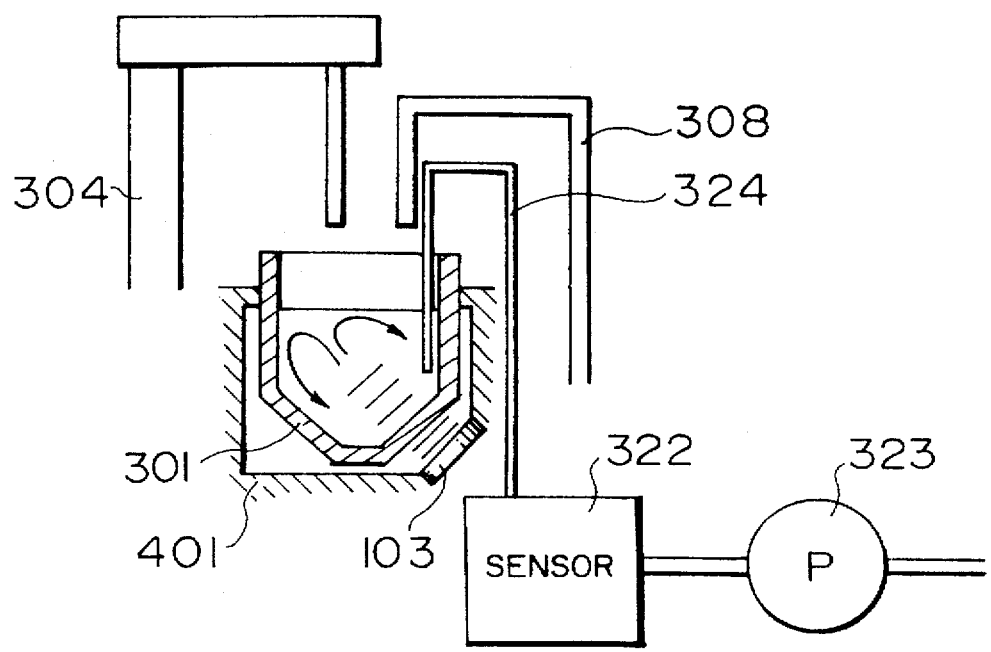
FIG. 7 is an enlarged fragmentary sectional view of another embodiment of the chemical analyzer according to the present invention.

The second embodiment of the chemical analyzer of the present invention will be described with reference to FIG. 7. The chemical analyzer shown in FIG. 7 includes an automatic sample pipetting mechanism 304, an automatic reagent pipetting mechanism 308, reaction vessels only one of which is shown at 301, a water container 401, a piezoelectric element 103 disposed at the bottom of the water container 401 to cause a circulating flow in the reaction vessel 301, a sensor 322 for measuring the physical properties of the sample contained in the reaction vessel 301, a tube 324 through which the sample is sucked from the reaction vessel 301 and introduced into the sensor 322, and a pump 323 for causing the sample to be sucked from the reaction vessel 301 and introduced into and moved past the sensor 322. The automatic sample pipetting mechanism 304 and the automatic reagent pipetting mechanism 308 are operated to feed predetermined quantities of a sample and a reagent solution into a reaction vessel 301. Simultaneously, the piezoelectric element 103 is energized to cause an acoustic straight flow in the reaction vessel, so that the sample and the reagent solution in the reaction vessel 103 are mixed together in a relatively short period of time. The piezoelectric element 103 is so positioned and oriented (angled) relative to the reaction vessel 301 that a circulating flow is caused in the vessel. The pump 323 is operated to suck the mixture of the sample and reagent solution from the reaction vessel 301 and feed the mixture to the sensor 322 so that the physical properties of the mixture are measured thereby.

The embodiment of the chemical analyzer described with reference to FIG. 7 effectively reduces the disadvantageous carry-over and, in addition, not only eliminates the operation step of inserting a stirring member into a reaction vessel but also saves the time needed for washing of the stirring member, to thereby assure a time-saving and efficient analysis.

It will be appreciated by those in the art that the chemical analyzer described with reference to FIG. 7 can be installed in combination with the chemical analyzer shown in FIG. 1.

What is claimed is:

1. In a chemical analyzer including a reaction vessel, means for feeding a sample into said reaction vessel through an upper opening thereof, means for feeding a reagent into said vessel through the upper opening thereof, and means for measuring a physical property of said sample during or after reaction of said sample with said regent, the improvement comprising sound wave generating means disposed in non-contact relationship with and outside of said reaction vessel for directing sound waves toward said reaction vessel in such a manner as to induce acoustic straight flow within said vessel at a level sufficient to mix said sample and said reagent.

2. A chemical analyzer according to claim 1, wherein the acoustic straight flow induced by the sound waves generated by said sound wave generating means causes convectional flow to occur in said reaction vessel for mixing said sample and said reagent in a circulatory motion.

3. A chemical analyzer according to claim 2, wherein said sound wave is of a frequency having a velocity of not less than $1\times10^{-4}$ m/s.

4. A chemical analyzer according to claim 1, further including means for determining a position of said sound wave generating means.

5. A chemical analyzer according to claim 1, wherein said sound wave generating means is disposed under to said reaction vessel and generates and directs the sound wave toward a bottom of said reaction vessel.

6. A chemical analyzer according to claim 5, wherein said sound wave generating means generates and directs the sound wave in a direction which is offset from a center of the bottom of said reaction vessel.

7. A chemical analyzer according to claim 5, wherein said sound wave generating means generates the sound wave such that an energy of the thus generated sound wave is converged at a point adjacent to a center of the bottom of said reaction vessel.

8. A chemical analyzer according to claim 7, wherein said sound wave generating means includes an acoustic lens operative to cause said sound wave to converge.

9. A chemical analyzer according to claim 1, wherein said sound wave generating means generates and directs the sound wave toward a side face of said reaction vessel.

10. In a chemical analyzer comprising a first turn table with a plurality of reaction vessels disposed thereon in a circular row, a second turn table with a plurality of sample containers disposed thereon in a circular row, each sample container containing a sample to be tested, a third turn table with a plurality of reagent containers disposed thereon in a circular row, each reagent container containing a quantity of reagent solution, sample feeding means operative to transfer a sample from one of said sample containers into one of said reaction vessels through an upper opening thereof, reagent feeding means operative to transfer a reagent solution from one of said reagent containers into said one reaction vessel through an upper opening thereof, and means for measuring a physical property of the sample contained in said one reaction vessel during or after reaction of said sample with a reagent contained in said one reaction vessel, the improvement comprising a sound wave generating means disposed in non-contact relationship with and outside each reaction vessel for directing sound waves toward the reaction vessel in such a manner as to induce acoustic straight flow within said vessel at a level sufficient to mix said sample and said reagent.

11. A chemical analyzer according to claim 10, wherein the acoustic straight flow induced by the sound waves generated by said sound wave generating means causes convectional flow to occur in said reaction vessel for mixing said sample and said reagent in a circulatory motion.

12. A chemical analyzer according to claim 11, wherein said sound wave is of a frequency having a velocity of not less than $1\times10^{-4}$ m/s.

13. A chemical analyzer according to claim 10, further including means for determining a position of said sound wave generating means.

14. A chemical analyzer according to claim 10, wherein said sound wave generating means is disposed under each reaction vessel and generates and directs the sound wave toward a bottom of the reaction vessel.

15. A chemical analyzer according to claim 14, wherein said sound wave generating means generates and directs the sound wave in a direction which is offset from a center of the bottom of each reaction vessel.

16. A chemical analyzer according to claim 14, wherein said sound wave generating means generates the sound wave such that an energy of the thus generated sound wave is converged at a point adjacent to a center of the bottom of each reaction vessel.

17. A chemical analyzer according to claim 16, wherein said sound wave generating means includes an acoustic lens operative to cause said sound wave to converge.

18. A chemical analyzer according to claim 10, wherein said sound wave generating means generates and directs the sound wave toward a side face of each reaction vessel.

19. A chemical analyzer according to claim 1, wherein said sound wave generating means directs sound waves towards a bottom of said reaction vessel at a location sufficient to induce one of counterclockwise and clockwise flow in said reaction vessel for mixing said sample and said reagent.

20. A chemical analyzer according to claim 1, wherein said sound wave generating means directs sound waves towards a bottom surface of said reaction vessel in such a manner as to induce at least two circulatory flows in said reaction vessel for mixing said sample and said reagent.

21. A chemical analyzer according to claim 20, wherein one of said two circulatory flows in a clockwise direction and the other of said circulatory flows in a counterclockwise direction.

22. A chemical analyzer according to claim 1, wherein said sound wave generating means directs sound waves towards a side surface of said reaction vessel in such a manner as to induce a circulatory flow in said reaction vessel which traverses an elliptical path, said elliptical path having an axis passing therethrough which is oriented at an acute angle with respect to a side wall of said reaction vessel.

23. A chemical analyzer according to claim 1, wherein said sound wave generating means directs sound waves so that said sample and reagent in said reaction vessel to be mixed are not uniformly subjected to a same magnitude of sound wave.

* * * * *